United States Patent
DiBiasi et al.

(10) Patent No.: US 10,441,730 B2
(45) Date of Patent: Oct. 15, 2019

(54) PEN NEEDLE ASSEMBLY FOR DELIVERING DRUG SOLUTION

(71) Applicant: Becton, Dickinson and Company, Franklin Lakes, NJ (US)

(72) Inventors: Michael A. DiBiasi, West Milford, NJ (US); Robert Banik, Long Valley, NJ (US); Roger W. Groskopf, Saddle Brook, NJ (US); Min Wei, Carmel, IN (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 671 days.

(21) Appl. No.: 14/172,288

(22) Filed: Feb. 4, 2014

(65) Prior Publication Data

US 2014/0188046 A1  Jul. 3, 2014

Related U.S. Application Data (62) Division of application No. 13/138,549, filed as application No. PCT/US2010/026129 on Mar. 3, 2010, now Pat. No. 9,445,838.
(Continued)

(51) Int. Cl.
*A61M 5/32* (2006.01)
*A61M 5/46* (2006.01)
(Continued)

(52) U.S. Cl.
CPC ....... *A61M 5/3293* (2013.01); *A61B 17/3496* (2013.01); *A61M 5/3202* (2013.01);
(Continued)

(58) Field of Classification Search
CPC . A61M 5/3202; A61M 5/3293; A61M 5/3294
See application file for complete search history.

(56) References Cited

U.S. PATENT DOCUMENTS 2,567,001 A * 9/1951 Watson ............... A61M 5/283
                                                      604/192
3,245,567 A * 4/1966 Knight ............... A61M 5/3202
                                                      215/253
(Continued)

FOREIGN PATENT DOCUMENTS

CN   1571685 A    1/2005
CN   1859937 A   11/2006
(Continued)

OTHER PUBLICATIONS

Japanese Official Notice of Final Decision of Rejection dated May 12, 2015.

*Primary Examiner* — William R Carpenter
(74) *Attorney, Agent, or Firm* — Dickinson Wright, PLLC (57) ABSTRACT

In one aspect, a pen needle assembly is provided herein which includes a hub, and a needle fixed to the hub, the needle having proximal and distal ends with a lumen extending therebetween. The needle extends distally from the hub to define an exposed length between the distal end of the needle and the hub in the range of about 5.0 to 9.0 mm. The hub defines a post formed about the needle, the post having a distally-facing first skin engaging surface. The exposed length of the needle extends distally from the first skin engaging surface. The hub also defines a distally-facing second skin engaging surface which at least partially circumscribes the first skin engaging surface. The second skin engaging surface being located proximally of the first skin engaging surface. Advantageously, a pen needle assembly is provided having two skin engaging surfaces which provide stability in achieving subcutaneous injections.

16 Claims, 5 Drawing Sheets

Related U.S. Application Data (60) Provisional application No. 61/209,050, filed on Mar. 3, 2009.

(51) Int. Cl.
*A61B 17/34* (2006.01)
*A61M 5/00* (2006.01)
*A61M 5/34* (2006.01)
*A61M 5/42* (2006.01)

(52) U.S. Cl.
CPC .............. *A61M 5/329* (2013.01); *A61M 5/46* (2013.01); *A61M 5/002* (2013.01); *A61M 5/347* (2013.01); *A61M 5/425* (2013.01); *Y10T 29/49815* (2015.01)

(56) References Cited

U.S. PATENT DOCUMENTS

| | | | |
|---|---|---|---|
| 3,491,575 A * | 1/1970 | Prendergast | B21D 24/00 72/349 |
| 3,491,757 A * | 1/1970 | Arce | A61M 5/34 604/242 |
| 3,961,622 A | 6/1976 | Edwards | |
| 4,009,716 A | 3/1977 | Cohen | |
| 4,430,080 A * | 2/1984 | Pasquini | A61M 5/348 604/240 |
| 5,098,389 A | 3/1992 | Cappucci | |
| 5,259,840 A * | 11/1993 | Boris | A61M 5/3213 604/110 |
| 5,931,817 A * | 8/1999 | Nguyen | A61M 5/002 604/192 |
| 5,941,857 A * | 8/1999 | Nguyen | A61M 5/3213 604/195 |
| 5,944,700 A * | 8/1999 | Nguyen | A61M 5/46 604/117 |
| 5,994,700 A | 8/1999 | Nguyen | |
| 5,971,966 A * | 10/1999 | Lav | A61M 5/002 206/365 |
| 5,980,495 A * | 11/1999 | Heinz | A61M 5/3202 128/919 |
| 6,387,074 B1 | 5/2002 | Horppu et al. | |
| 6,398,762 B1 | 6/2002 | Vetter et al. | |
| 6,986,760 B2 | 1/2006 | Giambattista | |
| 7,384,414 B1 * | 6/2008 | Marshall | A61M 5/326 604/198 |
| 7,556,615 B2 | 7/2009 | Pettis et al. | |
| 8,133,202 B2 | 3/2012 | Marsh | |
| 8,858,507 B2 * | 10/2014 | Nielsen | A61M 5/3202 604/162 |
| 2003/0050602 A1 | 3/2003 | Pettis et al. | |
| 2006/0032769 A1 * | 2/2006 | Erickson | A61M 5/002 206/365 |
| 2007/0005017 A1 | 1/2007 | Alchas | |
| 2007/0118077 A1 | 5/2007 | Clarke et al. | |
| 2007/0185460 A1 | 8/2007 | Vedrine et al. | |
| 2008/0045900 A1 | 2/2008 | Alchas et al. | |
| 2009/0069753 A1 * | 3/2009 | Ruan | A61M 5/3202 604/192 |
| 2009/0118678 A1 * | 5/2009 | Kawashima | A61M 5/3213 604/197 |
| 2009/0234288 A1 * | 9/2009 | Fischer | A61M 37/0015 604/117 |

FOREIGN PATENT DOCUMENTS

| | | |
|---|---|---|
| EP | 0903157 B1 | 6/2002 |
| EP | 1289587 B1 | 8/2005 |
| EP | 1930038 | 6/2008 |
| EP | 2440270 B1 | 4/2013 |
| EP | 2403566 B1 | 12/2015 |
| JP | 2001507956 A | 6/2001 |
| JP | 2002-360695 | 12/2002 |
| JP | 2003534105 A | 11/2003 |
| JP | 2005527249 A | 9/2005 |
| JP | 2006-517129 A | 7/2006 |
| WO | 0191837 A1 | 12/2001 |
| WO | 2005018722 | 3/2005 |
| WO | WO 2005049119 A1 * | 6/2005 .......... A61M 5/3213 |
| WO | 2007/061972 A2 | 5/2007 |

\* cited by examiner

PEN NEEDLE ASSEMBLY FOR DELIVERING DRUG SOLUTION

CROSS REFERENCE TO RELATED APPLICATION

This application is a division of U.S. patent application Ser. No. 13/138,549, filed Sep. 1, 2011, the entire disclosure of said prior application being incorporated herein by reference.

FIELD OF THE INVENTION

This invention relates to pen needle assemblies and, more particularly, to pen needle assemblies for delivering drug suspensions.

BACKGROUND OF THE INVENTION

Pen needle assemblies are well known in the art. To minimize discomfort, pen needle assemblies typically use needles in the range of 29 to 31 gauge. Where a pen injector is used to mix or reconstitute substances into a solution for delivery, thin needles, such as those in the range of 29 to 31 gauge, may be susceptible to clogging by agglomerations which result from re-suspension or incomplete mixing of the substances.

SUMMARY OF THE INVENTION

In one aspect, a pen needle assembly is provided herein which includes a hub, and a needle fixed to the hub, the needle having proximal and distal ends with a lumen extending therebetween. The needle extends distally from the hub to define an exposed length between the distal end of the needle and the hub in the range of about 5.0 to 9.0 mm. The hub defines a post formed about the needle, the post having a distally-facing first skin engaging surface. The exposed length of the needle extends distally from the first skin engaging surface. The hub also defines a distally-facing second skin engaging surface which at least partially circumscribes the first skin engaging surface. The second skin engaging surface being located proximally of the first skin engaging surface. Advantageously, a pen needle assembly is provided having two skin engaging surfaces which provide stability in achieving subcutaneous injections.

Objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying figures, in which.

Throughout the drawings, like reference numbers will be understood to refer to like parts, components and structures.

DETAILED DESCRIPTION OF THE EXEMPLARY EMBODIMENTS

With reference to the drawing figures, a pen needle assembly is shown and generally designated with the reference numeral 10. The pen needle assembly 10 is useable with various pen injectors for administering medicament. The pen needle assembly 10 is particularly well-suited to administer medicament which is mixed into a solution inside the associated pen injector, such as by re-constitution or mixing of two or more components (wet or dry), such as liquid and solid powder of particles, and/or medicament having particles in the formulation suspension. In either case, particles or particle agglomerations may be found in the medicament which may partially or wholly clog the lumen of a prior art administering needle. The pen needle assembly 10 provides an arrangement for delivering the suspension through minimizing the clogging of a needle lumen.

The pen needle assembly 10 generally includes a hub 12 and a needle 14. The needle 14 is fixed to the hub 12 by any known technique, e.g., adhesion, and includes a proximal end 16, a distal end 18 and a lumen 20 extending therebetween.

As used herein, the term "proximal", and derivatives thereof, shall refer to a direction away from a patient during use (i.e., the non-patient end), and the term "distal", and derivatives thereof, shall refer to a direction towards a patient during use (i.e., the patient end).

The hub 12 includes a body 22 which is preferably formed of a polymeric material, e.g. thermoplastic. The body 22 includes an open proximal end 24 which exposes the proximal end 16 of the needle 14. Preferably, the pen needle assembly 10 is removably mountable onto a medical pen injector I. This permits replacement of the pen needle assembly in allowing multiple injections to be administered by the pen injector I. To this end, mounting features 26 are formed on the body 22 for engaging cooperating mounting features F on the pen injector I. The mounting features 26 and F may be of any known type including cooperating threads, mechanical features (e.g., bayonet-type lock) and/or surface configurations, such as Luer surfaces. Alternatively, the hub 12 may be non-removably fixed to, or formed integrally with, the pen injector I. This configuration is useable with a single-use injector which is disposed of after one injection.

The proximal end 16 of the needle 14 is sized to access medicament M contained within the pen injector I with the hub 12 being mounted to the pen injector I. Typically, the medicament M will be housed within a reservoir or cartridge accommodated within the pen injector with a septum S forming a seal at the distal end thereof. The proximal end 16 is sufficiently sized to pierce through the septum S to access the medicament M with the hub 12 being mounted to the pen injector I. The medicament M may have clumps or agglomerations A floating therein.

The pen needle assembly 10 is configured to administer an injection of the medicament M into the subcutaneous region of a patient's skin. In addition, the pen needle assembly 10 is configured to minimize clogging in the lumen 20 resulting from insufficient depth of injection (i.e., clogging caused by attempted injection into the dermis/epidermis layer). With the pen needle assembly 10, an injection may be administered in the subcutaneous region with minimal concern for clogging of the lumen 20.

The needle 14 has an exposed length L1 which is defined between the distal end 18 of the needle 14 and the hub 12. The exposed length L1 is the portion of the needle 14 that extends distally from the hub 12 and that may be inserted into the patient during an injection. The exposed length L1 is in the range of about 5.0 to 9.0 mm.

In addition, a beveled surface 28 extends proximally from the distal end 18 of the needle 14 in which distal opening 30 is defined. The lumen 20 terminates at the distal opening 30. As will be appreciated by those skilled in the art, the beveled surface 28 may include various configurations including having multiple facets or bevels with the surfaces being of various configurations, including being partially or wholly planar and/or arcuate. The beveled surface 28 provides the distal end 18 of the needle 14 with a sharpened configuration for insertion into a patient.

Length L2 of the needle 14 corresponds to the length of needle 14 over which the beveled surface 28 extends. The length L2 is preferably in the range of 30%-60% of the exposed length L1. The length L2 is measured along the longitudinal axis of the needle 14 and not along the length of the beveled surface 28. The length L2, being in the range of 30%-60% of the exposed length L1, provides the distal opening 30 with an elongated shape that is minimally susceptible to clogging in the lumen 20 by any of the agglomerations A formed in the medicament M. It is additionally preferred that the needle 14 be of 25 gauge or larger in size, more preferably in the range of 20-25 gauge. With the needle 14 being of 25 gauge or larger in size, the lumen 20 is larger in cross-sectional size than a lumen of typical prior art pen needles (typical prior art pen needles being in the range of 29-31 gauge). With the needle 14 being of a larger gauge (25 gauge or larger in size), the lumen 20 is better configured to deliver the medicament M as a suspension (e.g., reconstituted or mixed solution) in being less susceptible to clogging of the lumen 20 by any of the agglomerations A formed in the medicament M.

In addition, to achieve a subcutaneous injection, it is preferred that the body 22 of the hub 12 define a post 32 about the needle 14. The post 32 includes a distally-facing first skin engaging surface 34, which is defined about the needle 14 continuously or discontinuously. The first skin engaging surface 34 acts as a stop against excessive insertion of the needle 14 into the patient. Preferably, the exposed length L1 is defined between the distal end 18 of the needle 14 and the first skin engaging surface 34. It is preferred that the post 32 be limited in its outer diameter so as to be smaller than the overall diameter or footprint of the body 22. Preferably, the first skin engaging surface 34 radiates outwardly from the needle 14 and terminates at an outer diameter D1, which more preferably is 0.121".

Figure 2:
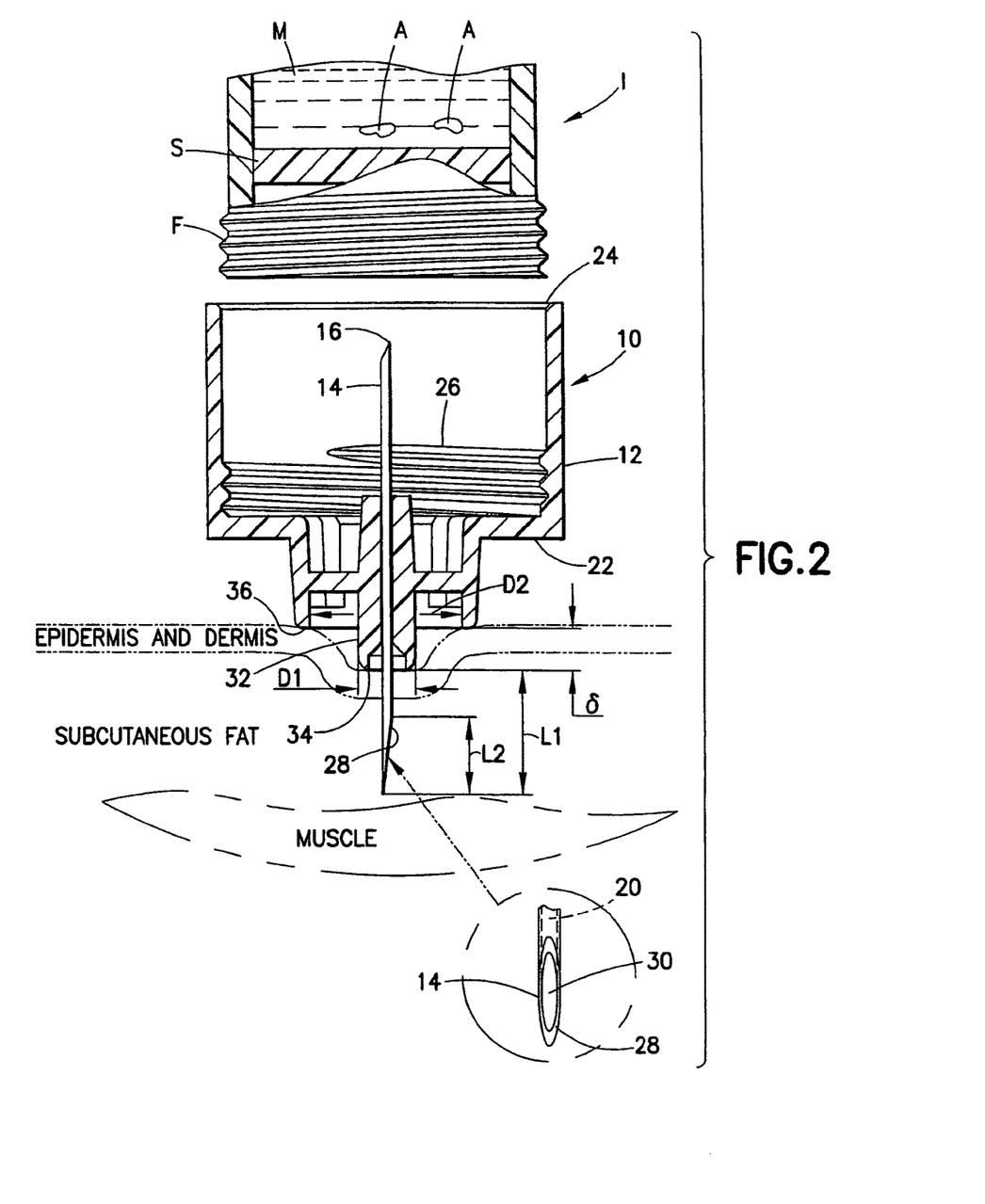
FIG. 2 is a cross-sectional schematic showing an injection formed with a pen needle assembly formed in accordance with the subject invention.

It is further preferred that the hub 12 defines a distally-facing second skin engaging surface 36 which is spaced radially outwardly from, and at least partially circumscribes, the first skin engaging surface 34. The second skin engaging surface 36 is located proximally of the first skin engaging surface 34 so as to define an offset 6 which is preferably in the range of 0.07"-0.10". As shown in FIG. 2, the first skin engaging surface 34 provides a focused point of contact against a patient's skin, which results in some deflection thereof. The second skin engaging surface 36 is spaced radially outwardly and rearwardly, by the offset 6, to provide a second hard stop against excessive insertion of the needle 14 into a patient's skin. The second skin engaging surface 36 provides stability to the pen needle assembly 10 during injection. Due to the limited diameter of the first skin engaging surface 34, there may be limited engagement with a patient's skin with insufficient stability for the injection. The second skin engaging surface 36 adds stability.

Figure 3:
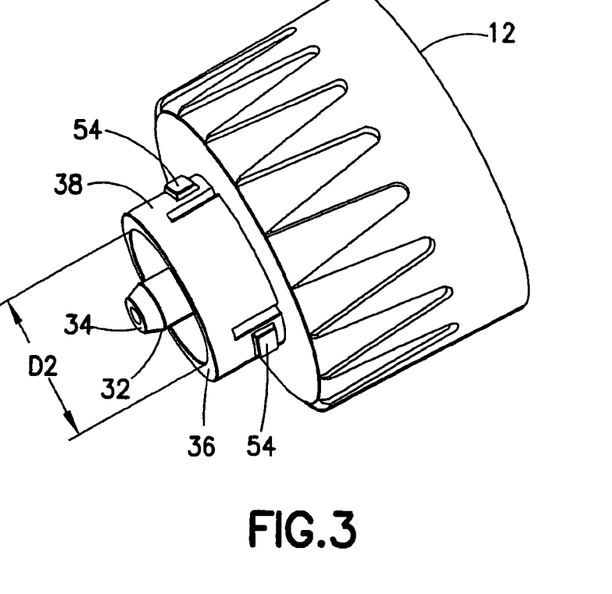
FIGS. 3 and 4 show different configurations of a second skin engaging surface usable with a pen needle assembly in accordance with the subject invention.
Figure 4:
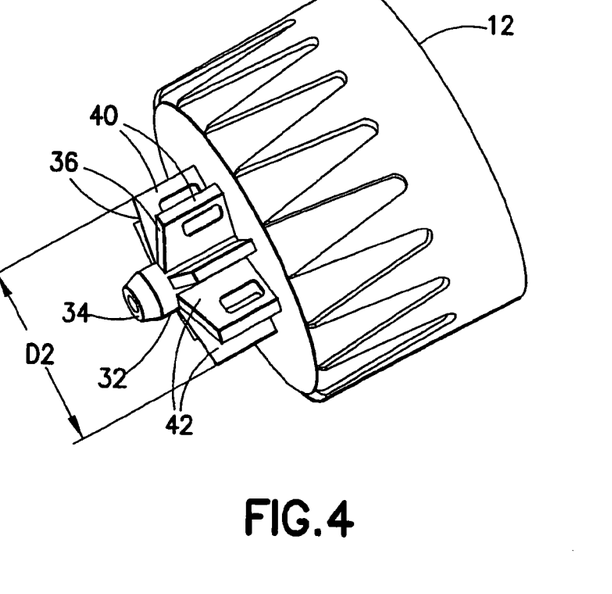

With reference to FIGS. 3 and 4, the second skin engaging surface 36 may be defined by various configurations which are continuous or discontinuous. With reference to FIG. 3, the second skin engaging surface 36 is defined with a monolithically formed annular shape at the end of wall 38 which completely circumscribes the post 32. The second skin engaging surface 36 preferably defines a diameter D2 of 0.340". In the embodiment of FIG. 3, the diameter D2 coincides with the inner edge of the second skin engaging surface 36. With reference to FIG. 4, the second skin engaging surface 36 may be defined over a series of fins 40 which radiate outwardly from the post 32. Spaces 42 are located between fins 40. The fins 40 are shaped and positioned so that collectively the second skin engaging surface 36 may be defined thereby which limits insertion of the needle 14 into the patient's skin, particularly to achieve subcutaneous injection. With the embodiment of FIG. 4, the find 40 may terminate radially outwardly at the diameter D2 so that the diameter D2 coincides with the outer edge of the skin engaging surface 36. In any regard, it is preferred that the diameter D2 be defined along a free edge of the second skin engaging surface 36 where, adjacent thereto, skin may be deflected or deformed. With the embodiment of FIG. 3, the diameter D2 coincides with an inner free edge of the second skin engaging surface 36, while in the embodiment of FIG. 4, the diameter D2 coincides with an outer free edge of the second skin engaging surface 36.

As shown in FIG. 2, the pen needle assembly 10 is intended for injections administered generally perpendicularly to a patient's skin.

Preferably, the ratio of the diameter D1 to the diameter D2 (D1/D2 ratio) is in the range of 0.25 to 0.58, more preferably the ratio is 0.36. It has been found that with these ratios, acceptable skin tension is created at the site of the injection with good stability. It has been found that if the diameter D2 is too large, insufficient skin tension is created and a shallow injection may result; if the diameter D2 is too small, there may be a lack of stability for injection, with less perpendicularity (which is desired) and a shallow injection resulting.

Figure 5:
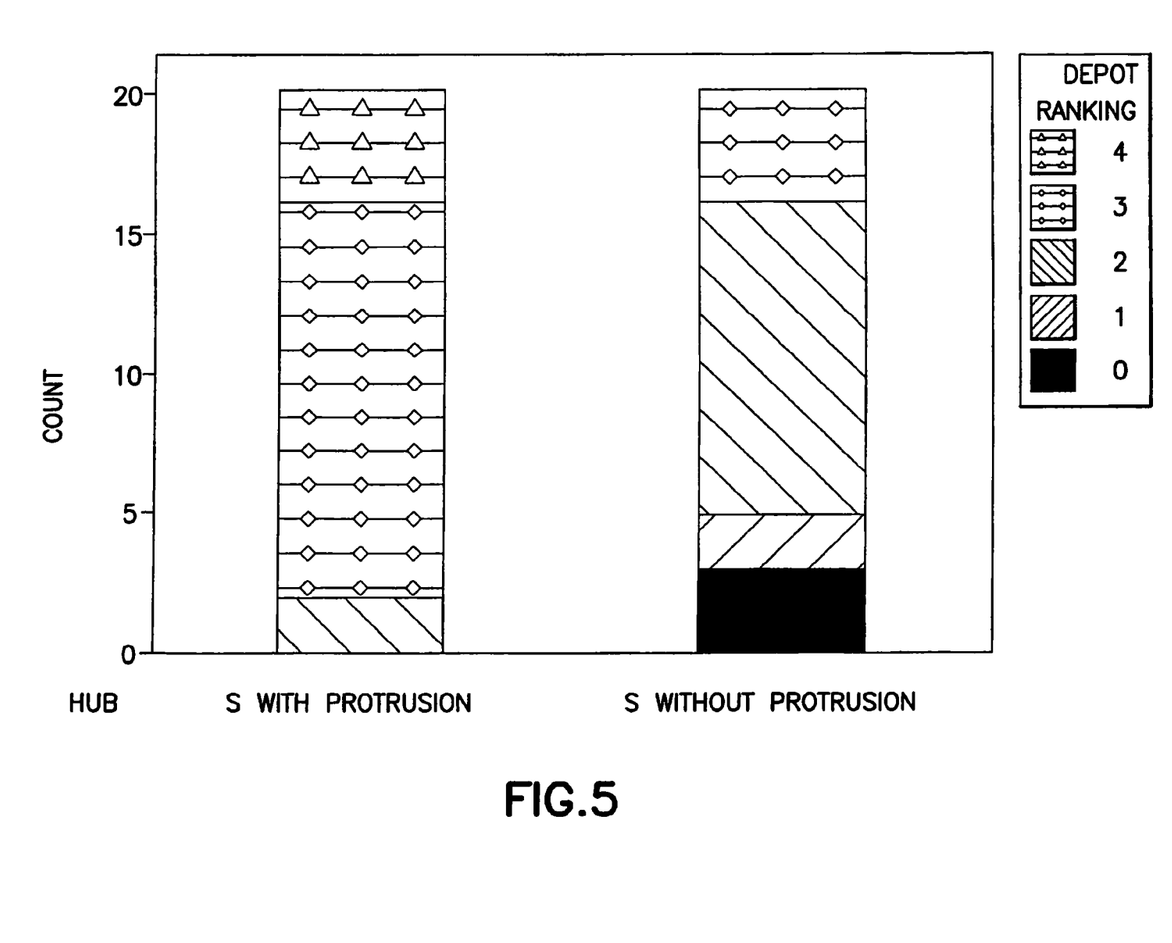
FIG. 5 is a chart showing test results.

With reference to FIG. 5, testing was conducted to evaluate the performance of subcutaneous injections with the pen needle assembly 10. The testing was conducted on a swine animal model, and it is believed that similar or same results will be achieved in injections on humans. The left hand column of FIG. 5 represents test results from using the pen needle assembly 10 as shown in FIG. 2, with the post 32 defining the first skin engaging surface 34 and the second skin engaging surface 36 being proximally set back by the offset 6. More specifically, the needle 14 used for this test was of a 23 gauge type with the offset 6 being 0.09", the diameter D1 being 0.121", the exposed length L1 being 7 mm, and the length L2 being 3 mm. In addition, the second skin engaging surface 36 had its inner edge coincide with the diameter D2 being 0.340".

With respect to the results, the injections were observed and ranked: a ranking of 4 corresponds to a deep subcutaneous injection; a ranking of 3 corresponds to a subcutaneous injection; a ranking of 2 corresponds to a shallow subcutaneous injection; a ranking of 1 corresponds to an intradermal injection; and, a ranking of 0 corresponds to a needle clogged by the dermis/epidermis. As can be seen in the left column, with the pen needle assembly 10 of the subject invention, repeated subcutaneous injections were achieved without clogging.

In particular, with reference to FIG. 5, using the pen needle assembly 10 of the subject invention, two shallow subcutaneous injections were achieved; fourteen subcutaneous injections were achieved; and, four deep subcutaneous injections were achieved. No clogging or intradermal injections were experienced.

The right band column of FIG. 5 represents a pen needle assembly which had the same parameters as discussed above with respect to the first set of test results but was without the offset 6 between the first and second skin engaging surfaces 34, 36 (i.e., the first and second skin engaging surfaces 34, 36 are coplanar). As can be seen, the majority of the injections were of the shallow subcutaneous type with a number of clogged needles also being achieved. In particular, three clogged needles were experienced; two intradermal injections were achieved; eleven shallow subcutaneous injections were achieved; and, four subcutaneous injections were achieved. The clogged needles resulted from excessively shallow needle insertion with failed injection into the dermis/epidermis; the needles were sufficiently clogged by the dermis/epidermis to not perform an injection.

As can be seen in FIG. 5, with the pen needle assembly 10 of the subject invention, repeated subcutaneous injections without clogging by the dermis/epidermis may be achieved. Subcutaneous injections as referred to herein are differentiated from shallow subcutaneous injections and deep subcutaneous injections. A subcutaneous injection is administered in a central area of the subcutaneous layer. It is desired to achieve insertion at this depth, rather than in a shallow or deep subcutaneous region where injections therein may coincide with the dermis/epidermis or muscle regions, respectively, of the patient. With the pen needle assembly 10 of the subject invention, medicament, which may be in suspension or prone to agglomeration, may be repeatedly delivered into the subcutaneous region with low susceptibility to clogging.

Figure 1:
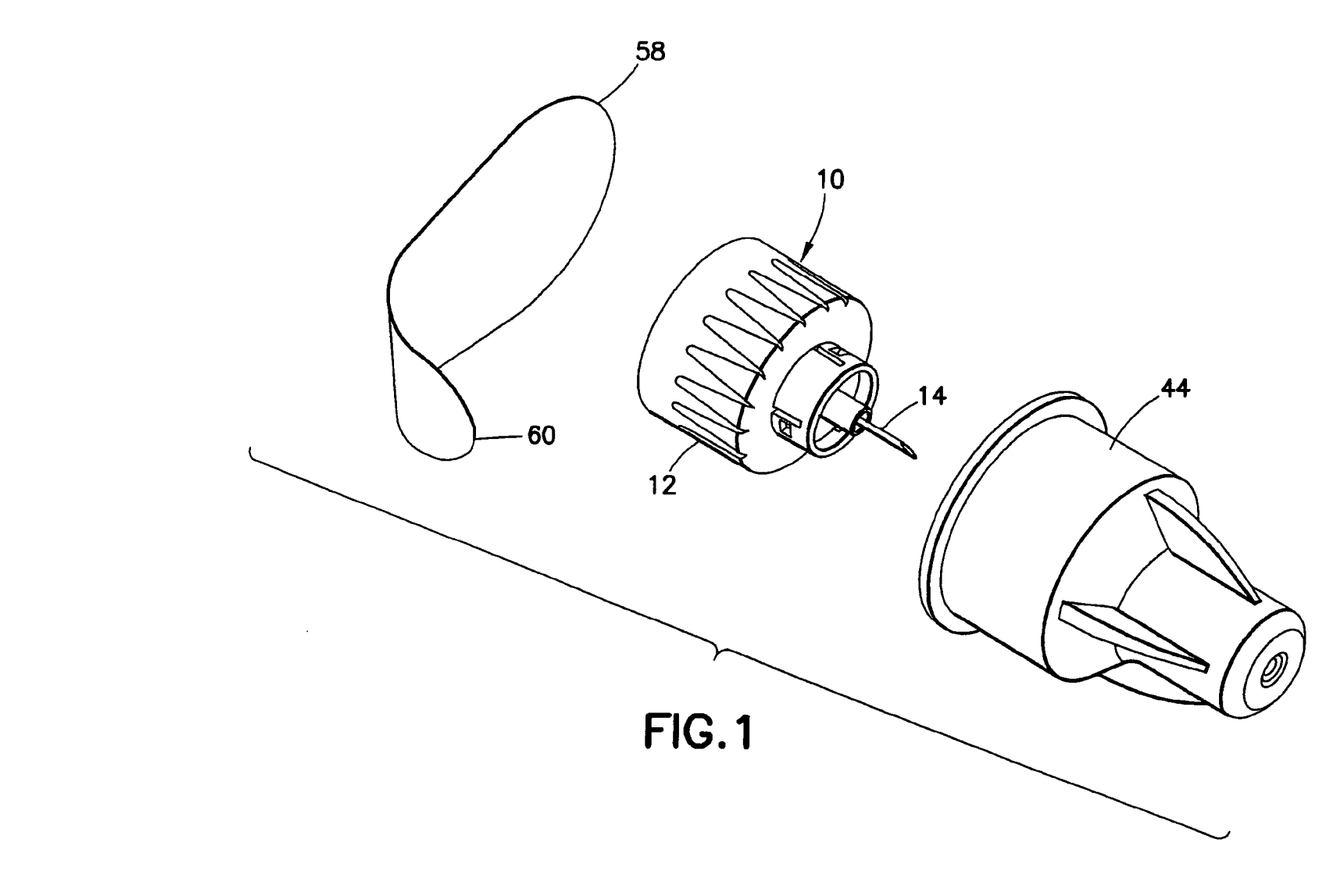
FIG. 1 is an exploded view showing a pen needle assembly formed in accordance with the subject invention along with usable packaging.
Figure 6:
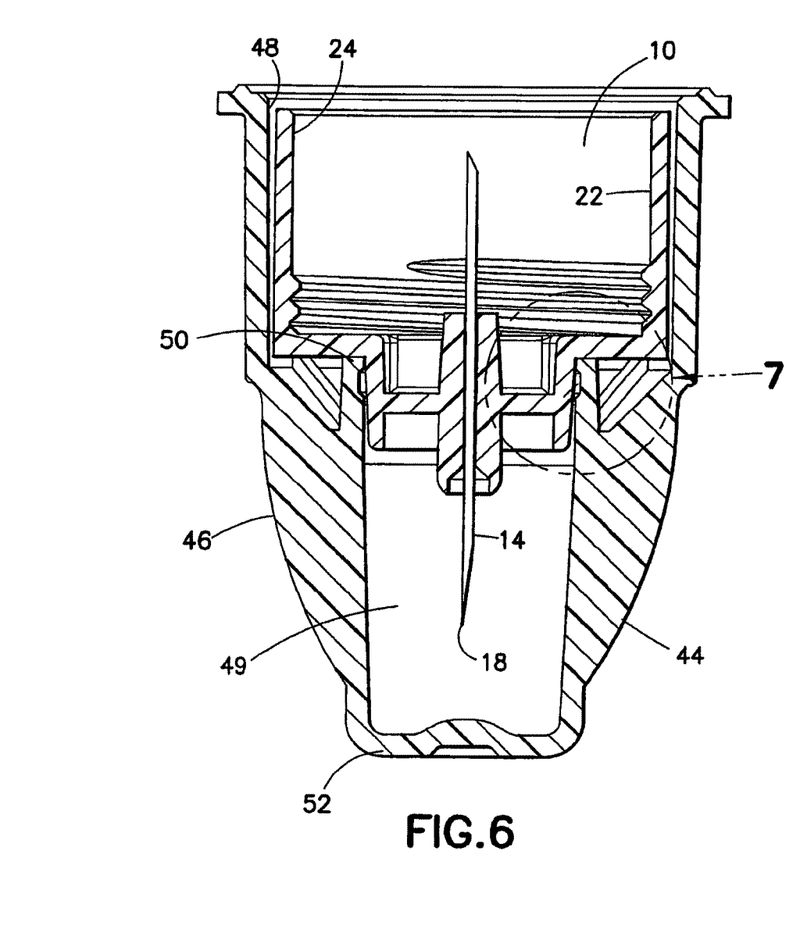
FIG. 6 is a cross-section showing a pen needle assembly formed in accordance with the subject invention in a packaged state.
Figure 7:
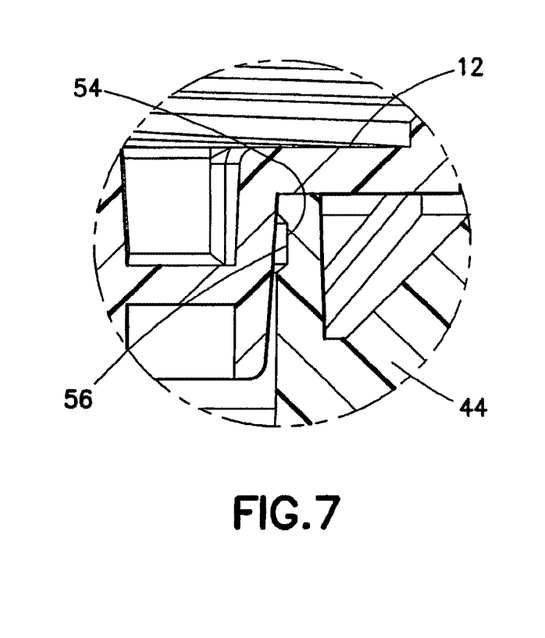
FIG. 7 is an enlarged view taken from section 7 of FIG. 6.

The pen needle assembly 10 may be packaged for use, as shown in FIGS. 1, 6 and 7. In particular, a rigid shell 44 may be provided sized to accommodate the pen needle assembly 10 therein with at least a portion of the needle 14, preferably at least the distal end 18 of the needle 14, being covered. Preferably, the shell 44 has a cup-shaped body 46 with an open proximal end 48 and an interior 49 into which the pen needle assembly 10 may be seated. To prevent excessive insertion of the pen needle assembly 10 into the body 46 during packaging, shoulder 50 may define a reduced-diameter region in the interior 49 which limits the extent of insertion of the pen needle assembly 10 into the body 46. As shown in FIG. 6, it is preferred that minimal clearance be defined between the shoulder 50 and the second skin engaging surface 36 to limit passage thereby of contaminants. Sterility of the exposed length L1 of the needle 14 may be better maintained in this manner. It is preferred that the proximal end 24 of the body 22 be exposed when seated in the body 46 such that the pen injector I may be mounted to the pen needle assembly 10 with it being contained within the shell 44. It is also preferred that the distal end 52 of the shell 44 be spaced from the distal end 18 of the needle 14 with the pen needle assembly 10 being seated within the body 46. In this manner, blunting of the needle 14 and inadvertent piercing of the shell 44 by the needle 14 may be avoided.

The shell 44 may be maintained on the pen needle assembly 10 in any known manner which permits releasable retainment of the shell 44 on the hub 12, including by frictional interengagement, frangible connection, mechanical connection and/or fusion or adhesion, such as spot fusion or adhesion. The force of retention for maintaining the shell 44 in the hub 12 should be great enough to prevent separation of the shell 44 from the hub 12 during normal transporting and storage, which may involve jarring or other force application to the combined package. It is preferred that the shell 44 be re-mountable onto the hub 12 after use (i.e., after an injection) to cover the needle 14 in a post-use state. It is preferred that the configuration for releasable retainment permit re-mounting of the shell 44 and retention thereof on the hub 12. In this manner, the pen needle assembly 10 may be disposed of with the needle 14 in a used state being covered.

Preferably, as shown in FIG. 3, one or more resilient snaps 54 may be provided on the hub 12 which are received in snap engagement in corresponding snap recesses 56 formed on the shell 44, as shown in FIGS. 6 and 7. In a packaged state, as shown in FIGS. 6 and 7, the inherent resilience of the interengagement of the snaps 54 and the snap recesses 56 provide sufficient retaining force for holding the shell 44 onto the hub 12. The inherent resilience, however, is surmountable to permit disengagement of the snaps 54 from the snap recesses 56 in allowing separation of the shell 44 from the hub 12 to permit use. The shell 44 may be re-mounted onto the hub 12 after use with the snaps 54 and the snap recesses 56 being caused to re-engage. As will be appreciated by those skilled in the art, the snaps 54 and the snap recesses 56 may be formed on the hub 12/and or the shell 44.

It is preferred that an audible signal be generated upon the shell 44 being properly mounted onto the hub 12 in entering the retained state therewith. For example, the snaps 54 may have sufficient inherent resilience so as to generate a click, or other audible signal, upon snap engaging the snap recesses 56.

The pen needle assembly 10 is preferably mounted onto the pen injector I prior to any necessary preparation of the medicament M, such as by mixing or reconstituting components found in the pen injector I. It is preferred that a sufficiently strong retaining force be provided for the shell 44 on the hub 12 so as to retain the shell 44 on the hub 12 during any shaking or other agitation of the pen injector I in preparing the medicament M. The agitation may include tapping the shield 44 against a surface. The retaining force needs to be sufficiently strong to prevent separation under such conditions. Subsequent manual removal of the shield 44 from the hub 12, however, must be permitted to allow priming of the needle 14 and subsequent injection.

The inherent resilience of the retaining force may also be sufficiently strong to permit rotational force applied to the shell 44 to be transmitted to the hub 12 in mounting the pen needle assembly 10 onto the pen injector I, particularly where the mounting features 26 and F are cooperating threads.

A barrier sheet or film 58 may be also provided to be applied in removable securement across the proximal end 48 of the shell 44 to wholly enclose, with the shell 44, the pen needle assembly 10 in a packaged state. Preferably, the sheet 58 provides a sterility barrier. The pen needle assembly 10 may be sterilized prior to packaging within the shell 44 or while inside the shell 44. The sheet 58 may be secured to the shell 44 using known techniques, such as adhesion or fusion. A grip 60 may be provided to extend from the sheet 58 to facilitate removal thereof.

The foregoing embodiments and advantages are merely exemplary and are not to be construed as limiting the scope of the present invention. The description of exemplary embodiments of the present invention is intended to be illustrative, and not to limit the scope of the present invention. Various modifications, alternatives and variations will be apparent to those of ordinary skill in the art, and are intended to fall within the scope of the invention as defined in the appended claims and their equivalents.

What is claimed is:

1. A combination for use with a medical pen injector which requires shaking to prepare a medicament contained therein for administration to a patient, said combination comprising:
    a medical pen injector adapted to receive a pen needle assembly;
    the pen needle assembly including:
    a hub having a post defined around a needle and having a first distally facing skin engaging surface, the hub further comprising an annular wall formed monolithically with the hub, the annular wall spaced radially away from the post with a second distally facing skin engaging surface, the annular wall having a cantilevered resilient snap formed in the annular wall and adjoined thereto, wherein the cantilevered resilient snap is shaped to flex where the cantilevered resilient snap adjoins the annular wall; and,
    wherein said needle is fixed to said hub, and,
    a shell comprising a snap recess, said shell configured for releasable retainment on said hub when said cantilevered resilient snap engages said snap recess, said shell being retainable on said hub with said shell covering at least a portion of said needle, the force of said retainment being provided by the engagement of the cantilevered resilient snap within the snap recess, the cantilevered resilient snap having a resilience sufficient to maintain said shell retained on said hub with said pen needle assembly being mounted to a medical pen injector with the medical pen injector being shaken to prepare a medicament contained therein for administration to a patient.

2. The combination according to claim 1, wherein said needle extends distally from said hub to define an exposed length in the range of about 5.0 to 9.0 mm.

3. The combination according to claim 1, wherein said shell includes a cup-shaped body having an interior formed to accommodate said pen needle assembly.

4. The combination according to claim 3, wherein said body includes a distal end, said distal end being spaced from said needle with said pen needle assembly being accommodated in said body.

5. The combination according to claim 1, further comprising a barrier sheet or film removably secured to said shell to wholly enclose said pen needle assembly with said shell.

6. The combination according to claim 5, further comprising a grip connected to said barrier sheet or said film to facilitate removal thereof.

7. The combination according to claim 1, wherein rotational movement of said shell is transferrable to said hub by contact between said resilient snap and said snap recess when said shell is in releasable retainment with said hub.

8. The combination according to claim 1, further comprising an audible indication when said at least one recess receives said at least one cantilevered resilient snap to indicate said shell being properly mounted on said hub.

9. The combination according to claim 1, wherein said shell is reconnectable to said hub after removal.

10. The combination according to claim 9, wherein a proximal end of said needle is covered by said shell when said shell is reconnected to said hub.

11. The combination according to claim 1, wherein said hub is internally threaded to facilitate connecting to the pen injector.

12. A method of preparing a medicament for administration, comprising the steps of:
    connecting a hub comprising a post defined around a needle and having a first distally facing skin engaging surface, the hub further comprising an annular wall formed monolithically with the hub, the annular wall spaced radially away from the post with a second distally facing skin engaging surface, the annular wall having a cantilevered resilient snap formed in the annular wall and adjoined thereto, wherein the cantilevered resilient snap is shaped to flex where the cantilevered resilient snap adjoins the annular wall and is disposed within a shell comprising a snap recess engaged with said cantilevered resilient snap to a medical pen injector containing the medicament;
    shaking the medical pen injector after connecting the hub thereto to prepare the medicament;
    retaining the she on the hub by the engagement of the cantilevered resilient snap within the snap recess, wherein the cantilevered resilient snap resilience is sufficient to maintain the shell on the hub when shaking the medical pen injector to prepare the medicament; and
    removing the shell from the hub after shaking the medical pen injector.

13. The method of preparing a medicament for administration according to claim 12, wherein said connecting step comprises rotating the shell to threadably engage the hub with the medical pen injector.

14. The method of preparing a medicament for administration according to claim 12, further comprising reconnecting the shell to the hub after removal to cover a proximal end of a hub needle.

15. The method of preparing a medicament for administration according to claim 14, further comprising generating an audible indication when reconnecting the shell to the hub to indicate that the shell is properly connected to the hub when the cantilevered resilient snap engages the snap recess.

16. The method of preparing a medicament for administration according to claim 12, further comprising removing a sterility barrier connected to the shell prior to connecting the hub to the medical pen injector.

* * * * *